United States Patent
Peterzell et al.

(10) Patent No.: US 6,960,962 B2
(45) Date of Patent: Nov. 1, 2005

(54) LOCAL OSCILLATOR LEAKAGE CONTROL IN DIRECT CONVERSION PROCESSES

(75) Inventors: Paul E. Peterzell, San Diego, CA (US); David Maldonado, Chula Vista, CA (US); Kevin Gard, San Diego, CA (US); Puay Hoe See, San Diego, CA (US); Jeremy Dunworth, Cardiff, CA (US); Gurkanwal Sahota, San Diego, CA (US)

(73) Assignee: Qualcomm Inc., San Diego, CA (US)

( * ) Notice: Subject to any disclaimer, the term of this patent is extended or adjusted under 35 U.S.C. 154(b) by 0 days.

(21) Appl. No.: 10/020,607

(22) Filed: Dec. 10, 2001

(65) Prior Publication Data

US 2003/0040292 A1 Feb. 27, 2003

Related U.S. Application Data

(63) Continuation of application No. 09/797,745, filed on Mar. 1, 2001, now abandoned.
(60) Provisional application No. 60/261,714, filed on Jan. 12, 2001.

(51) Int. Cl.[7] .......................... H03B 21/01; H03L 7/00; H04B 1/00
(52) U.S. Cl. .......................... 331/40; 331/25; 331/37; 331/41; 331/74; 455/313

(58) Field of Search .............................. 331/14, 16, 17, 331/25, 37, 40, 41, 74, 76; 455/313, 318

(56) References Cited

U.S. PATENT DOCUMENTS 5,307,029 A * 4/1994 Schenk ........................ 331/37
6,009,312 A    12/1999 Dolman

FOREIGN PATENT DOCUMENTS

| EP | 0798880 | 3/1997 |
| WO | 0031885 | 6/2000 |
| WO | 0052840 | 9/2000 |

* cited by examiner

Primary Examiner—David Mis
(74) Attorney, Agent, or Firm—Philip R. Wadsworth; Charles D. Brown; George C. Pappas

(57) ABSTRACT

A system and method for generating a local oscillator (LO) frequency in a zero intermediate frequency (IF) receiver or transmitter is presented. A signal is received from a voltage controlled oscillator (VCO). The signal has a VCO frequency. The VCO frequency is divided by a number N to produce a signal having a divided-down frequency. The signal having the VCO frequency is then mixed with the signal having the divided-down frequency to produce an output signal having an output frequency. Local oscillator leakage is reduced. Thus, the receiver or transmitter may operate in multiple wireless communication bands and modes and meet the associated specifications.

49 Claims, 8 Drawing Sheets

US 6,960,962 B2

LOCAL OSCILLATOR LEAKAGE CONTROL IN DIRECT CONVERSION PROCESSES

RELATED APPLICATIONS

This application claims priority to Provisional application No. 60/261,714, filed on Jan. 12, 2001. This application is a continuation of U.S. patent application Ser. No. 09/797,745 filed on Mar. 1, 2001, now abandoned.

BACKGROUND

1. Field

This invention relates in general to wireless communications. Specifically, this invention relates to systems and methods for direct conversion transceivers.

2. Background and Related Art

The field of communications has experienced a tremendous growth due in large part to the improved capabilities of wireless devices. Wireless devices employ radio waves to enable distant communications without the physical constraints of wire-based systems. Information, such as voice, data, or paging information, is conveyed by radio waves transmitted over predetermined frequency bands. Allocation of available frequency spectra is regulated to ensure that numerous users may communicate without undue interference.

Information to be transmitted from a source to a destination is seldom acquired in a format that is ready for radio transmission. Typically, a transmitter takes an input signal and formats it for transmission in a predetermined frequency band. The input signal, also referred to as a baseband signal, modulates a carrier in the desired frequency band. For example, a radio transmitter that receives an audio input signal modulates a carrier frequency with the input signal.

A corresponding remote receiver tuned to the same carrier frequency as the transmitter must receive and demodulate the transmitted signal. That is, the remote receiver must recover the baseband signal from the modulated carrier. The baseband signal may be directly presented to a user or may be further processed prior to being presented to the user. Many consumer wireless devices, such as radios, televisions, and pagers, are solely receivers.

Transceivers are wireless devices that integrate a transmitter and receiver in a single package. Transceivers enable nearly instantaneous two-way communications. Examples of transceivers include two-way radios, walkie-talkies, two-way pagers, and wireless phones.

Several figures-of-merit are important in assessing the effectiveness of a receiver design. Sensitivity determines the ability of a receiver to detect a weak signal. Receiver sensitivity must be such that the receiver can detect the minimal discernible signal (MDS) from background noise. Noise represents random fluctuations in voltage and current. The MDS a receiver-specific measure of sensitivity that incorporates the bandwidth of a given system. Receiver selectivity on the other hand, indicates the protection afforded a receiver from off-channel interference. The greater the selectivity, the better the receiver can reject unwanted signals.

Desense is a reduction in a receiver's overall sensitivity due to man-made or natural radio frequency interference (RFI). Desense occurs when a very strong interfering signal overloads the receiver and makes the detection of weaker signals more difficult. The desensitization characteristic of the receiver determines its ability to operate successfully under strong interferers, such as jammers.

The noise figure is another key measure of a receiver's performance. The noise figure degrades, that is, increases, at each successive stage in the receive path. Amplification or attenuation techniques may be applied within a receiver to achieve an acceptable noise figure. Noise, along with distortion, determines signal to noise and distortion (SINAD), a ratio in decibels which describes a receiver's performance in the presence of noise.

Distortion is the presence of unwanted signals at the output of devices in the RF path of a receiver. Distortion may include harmonic distortion, intermodulation distortion, and cross-modulation distortion. Harmonic distortion occurs when the desired input signal is large enough to compress the receiver and is typically measured at the baseband output as a function of frequency offset from the desired signal and as a function of the desired signal power. Crossover distortion occurs when the amplitude-modulated component from the transmitter (e.g., a CDMA wireless phone) is transferred to another carrier (jammer) at the output of the device (LNA output). The most common form of distortion is intermodulation distortion (IMD).

Intermodulation distortion is the result of two or more signals mixing together to produce additional unwanted distortion within the signal bandwidth. For two inputs, the intermodulation products occur at the sum and difference of integer multiples of the original frequencies. That is, for two input signals having frequencies $f_1$ and $f_2$, the output frequency components can be expressed as $mf_1 \pm nf_2$, where m and n are integers $\geq 1$. The order of the intermodulation product is the sum of m and n. "Two tone" third order components ($2f_1-f_2$ and $2f_2-f_1$) can occur at frequencies near the desired or interfering signals and thus cannot be easily filtered. Higher order intermodulation products have lower amplitude; as such, they are less problematic. Second order intermodulation jamming products may be generated at baseband frequencies if the tone spacing is within half of the signal bandwidth.

FIG. 1 is a graph plotting the levels of fundamental, second order, and third order IMD components against input level. Theoretical points where the second order and third order levels intercept the fundamental are known as the second order intercept point (IP2 or SOI) and third order intercept point (IP3 or TOI). The IIP2 of a receiver is the input level second order intercept point. The IIP3 is the input level third order intercept point.

The third order intercept point and noise figure of a receiver are directly related to the receiver's dynamic range. The dynamic range defines the range of signals that the receiver can handle within the specified performance of the receiver, that is, the range over which the receiver can produce an accurate output with acceptable SINAD. Specifically, for a baseband receiver, such as an analog-to-digital converter, the dynamic range may be represented as spurious free dynamic range (SFDR), which ranges from the noise floor of the device to the maximum signal before clipping occurs.

Local oscillator (LO) leakage occurs when an LO signal leaks to the receiver input. Such leakage may be transmitted by the transceiver antenna as spurious emissions, which may interfere with other devices. In addition, LO leakage may be reflected back into the receiver itself and may desense the receiver if not removed prior to demodulation.

Jammer leakage occurs when a jammer signal leaks to an LO input or output of a device within a receiver. Such leakage may mix with the jammer signal to produce undesired signals, such as DC signal levels that are proportional to the amplitude modulation (AM) component of the jammer signal. AM jammer signals may be located at any frequency within a receive frequency band.

Low-frequency flicker (1/f) noise is caused by defects in the emitter-base junction of bipolar junction transistors. Although typically small, flicker noise and other such noise may need to be removed in a receiver in order to maintain signal integrity at baseband.

Isolation is the ratio (in dB) of the power level applied at one port of a device to the resulting power level at the same frequency appearing at another port. Reverse isolation, which is the inverse (reciprocal) of isolation, is a figure-of-merit for receiver components. Reverse isolation is a measure of how much energy injected into an output port makes it back into the input source. To achieve low LO and jammer leakage, high reverse isolation is desired.

The 1 dB compression point of an amplifier is a measure of the output power level when the amplifier gain is 1 dB lower than the small signal gain. The saturation point of an amplifier is a measure of the maximum output power capability of the amplifier. These figures-of-merit are illustrated in FIG. 1.

The above figures-of-merit and signal phenomena should be considered when designing wireless communication devices. More generally, the wireless communications landscape has been dominated by Code Division Multiple Access (CDMA), a form of spread spectrum, or broadband, communications in which radio signals are spread over a very wide bandwidth. CDMA technologies have been the basis for many modulation standards, such as CDMA (IS-95 and CDMA2000) and WCDMA (IMT2000). Each of these modulation or air-interface standards operates in many radio frequency bands, including Cellular (Japan Cellular and US Cellular), PCS (Personal Communications System in US and Korean bands), and IMT (International Telecommunications Union). Other modulation standards include FM (frequency modulation, IS-19), GSM (Global System for Mobile Communications), US-TDMA (IS-136), GPS (Global Positioning System), Wireless LAN (802.11), and Bluetooth.

Frequency bands have been allocated to various communications modes. For wireless transceivers, the US PCS receive (RX) frequency band is 1930–1990 MHz, and the associated transmit (TX) frequency band is 1850–1910 MHz. The US Cellular receive frequency band is 869–894 MHz, and the associated transmit frequency band is 824–849 MHz. Similarly, receive and transmit frequency bands are allocated to Japan Cellular, IMT, and Korean PCS.

Communications standards set forth specifications that wireless communication devices must meet. For instance, spurious emissions, sensitivity, jamming (two-tone intermodulation and single-tone desense), and residual sideband specifications must be met.

Wireless communications have not yet been standardized on an international, or even intranational, basis. Existing technologies have recognized that a transceiver that can operate in more than one band, or in more than one mode, has increased portability. In particular, dual band handsets operate on two frequency bands. For instance, a dual band CDMA handset can operate on both the 800 MHz (US Cellular) and 1.9 GHz (US PCS) frequency bands. If base stations operating on these two bands use the CDMA standard, then a mobile unit having a dual band CDMA handset may obtain service from either or both of these base stations. Further, a dual mode CDMA/FM handset may operate in both CDMA and FM modes. Yet, given the current multiplicity of modulation standards and associated frequency bands, dual mode and dual band phones offer subscribers at most a limited compatibility with communications systems of the world.

FIG. 2 is a high-level block diagram of a conventional dual downconversion receiver. Receiver 101 incorporates the super heterodyne architecture. In particular, a received RF signal 11 is conveyed along an RF signal path and preprocessed (stage 1). The preprocessed RF signal 13 is first translated, or downconverted, to a signal 15 having an intermediate frequency (IF) (stage 2). The IF signal 15 is then downconverted again to a baseband signal 17, which includes an "in-phase" (I) and "quadrature" (Q) phase component (stage 3). The I and Q baseband signal components vary in phase by 90°. The I and Q components are then sent to other portions of receiver 101, such as a baseband processor (stage 4), to be further processed. Similarly, in a dual upconversion transmitter, analog I and Q baseband signals are first upconverted to an IF signal, and the IF signal is then upconverted to a transmitted RF signal.

FIG. 3 illustrates receiver 101 in more detail. Receiver 101 has a number of inherent benefits. For example, the design offers excellent sensitivity and selectivity, an extended signal dynamic range, flexible frequency planning, and a lower dynamic range and current consumption for elements in receiver 101 after IF filters 70. In addition, phase and amplitude matching between the I and Q channels 106, 107 may be achieved more easily because the IF signal is at a lower frequency range. In view of these benefits, receiver 101 is well-suited for multi-mode and multi-band applications, wherein received RF signals—modulated in multiple modes and conveyed in multiple frequency bands—may be processed.

To support multiple bands and modes of operation, receiver 101 must include some mode-specific components. For instance, in a multi-band receiver, an individual RF signal path is typically required for each frequency band. In a multi-mode receiver, individual baseband paths may be required for each mode depending on jammer dynamic range requirements.

In conventional receivers such as receiver 101, the IF signal path typically includes amplifiers, filtering, and automatic gain control (AGC) circuitry. As such, receiver 101 can eliminate out-of-signal-band noise and jammers and can compensate for varying signal power and receiver gain changes. In a multi-mode receiver, filtering of IF signals is mode-specific. Therefore, receiver 101 has one IF filter 70 per mode. For instance, a receiver in a dual mode phone includes two IF SAWs (surface acoustic wave filter). For a receiver which supports the CDMA 1X, CDMA 3x, WCDMA, GSM, FM, Bluetooth, and GPS modes, four to six SAWs and 1 discrete LC filter may be required in the IF signal path.

The need for an IF filter for each mode is a significant drawback of receiver 101. Each IF filter increases the cost of the receiver, the number of critical parts, and the board area of the receiver. Because each IF filter may have high loss, an IF pre-amp or AGC may also be needed. An IF voltage controlled oscillator (VCO) and phase-locked loop (PLL) 65 are also needed to generate a local oscillator (LO) frequency, which is inputted to IF mixer 60. Additional drawbacks of receiver 101 include the need for a switch matrix or multiple IF amplifiers and AGC modules, the need for a low-loss RF bandpass filter (BPF) to reduce undesired sideband noise, and the need for additional IF mixers. Thus, the IF stage of a dual downconversion receiver increases cost, design complexity, and circuit board area of such receivers.

FIG. 4 is a block diagram of a direct downconversion, or zero IF, receiver 200. In direct downconversion receivers, a received RF signal 201 is directly downconverted to a baseband signal 225. Similarly, in a direct upconversion, or zero IF, transmitter, a baseband signal is directly upconverted to a transmitted RF signal. In receiver 200, the received RF signal is mixed with a local oscillator (LO) frequency to produce a baseband signal. Because it does not incorporate an IF signal path, receiver 200 eliminates cost, board area, and power consumption associated with IF components, which include IF SAWs, LC matching and discrete filters, a pre-amp, AGC, IF mixers, and the IF VCO and PLL. Further, less part-to-part and temperature variation occurs.

The design of receiver 200 allows for more signal processing, such as channel selectivity filtering, to occur in the baseband analog or digital domain via integrated circuits, thus enabling RF and analog portions of receiver 200 to be more generic in nature. Since the AGC is digital, simplified calibration, or even no calibration, may be required. For certain modes of operation, such as GPS, Bluetooth, and GSM, receiver 200 may not require an RF filter because a primary purpose of that filter is to reduce cross-modulation in CDMA Cellular and PCS modes. However, the GPS mode may require an RF filter if GPS-modulated signals are simultaneously received with other modulated signals.

Despite the above advantages, direct downconversion has not been widely incorporated into wireless phones. The reason is that it is very difficult to achieve key receiver design goals while achieving the proper dynamic range for the receiver. Design goals for receivers such as receiver 200 include achieving high gain and a low noise figure, high IIP3 and IIP2 values, and low power consumption. A multi-mode and multi-band receiver may require a very wide dynamic range. Accordingly, it is even more difficult to achieve these design goals for such a receiver.

More specifically, local oscillator (LO) leakage and jammer leakage into the I and Q mixer LO ports cause significant problems in direct downconversion receivers. For Cellular and PCS, the spurious emissions requirements are particularly stringent. As such, higher reverse isolation is needed. Additionally, in a direct downconversion receiver, LO leakage that is reflected back into the receiver itself, as well as jammer leakage to the LO port of the I and Q mixers, may be processed by the direct downconversion circuitry. As such, an undesired DC offset voltage may appear at the output of the mixer along with the desired baseband signal, which may also contain baseband spectral components. Accordingly, the DC offset must be removed to ensure that the signal-to-noise ratio is sufficiently high.

In CDMA, sensitivity is tested with a signal set to a level such that a certain frame error rate (FER) is met. IS-98 specifies that the device under test must meet a sensitivity level of −104 dBm (signal power) with less than 0.5% FER. The intermodulation test is conducted with a signal level set to −101 dBm (3 dB above the sensitivity test) with two tones at an offset relative to the RF signal (−43 dBm/tone at offsets that generate an in-band distortion product, or typically ±900 and ±1700 kHz) with less than 1% FER. Depending on the frequency band, there may be differences in the power levels tested and frequency offsets for the jammers. For the single-tone desense test, the jammer level at the RF port of the I and Q mixers is larger than the signal level by 71 dB at >=900 kHz offset.

The jammer power may leak to the LO port of each mixer and mix with the jammer level at the mixer RF port to produce a DC level that is proportional to the amplitude of the RF jammer. Typically, the jammer is generated by the forward link of a base station in a competing wireless system. The jammer power may change as a function of the modulation used or fading. The worst jammer may have amplitude modulation comparable to the desired signal bandwidth. As such, the AM component falls on top of any signal energy at baseband after downconversion and cannot be removed with baseband filtering. This problem is exacerbated as the jamming RF signal increases. If the jamming RF signal increases by 10 dB, for example, the baseband distortion increases by 20 dB. This baseband distortion can actually be greater than a two-for-one slope if both the RF to LO isolation of the RF mixers, which affects self-mixing of jammers, and the IIP2 of the RF mixers, which represents second order distortion effects, are poor.

Further, the jammer and LO leakage requirements for mixers in a direct downconversion receiver are very demanding. Because such a receiver lacks IF filtering, the dynamic range of the receiver baseband elements may need to be increased by 30 dB or more, depending on the degree of baseband analog filtering, and part-to-part, frequency, and temperature variations in gain. Residual sideband specifications for various modulation standards must also be met. Since such a receiver has less gain before its baseband stage, flicker noise at baseband has a greater effect on the ability of the receiver to process FM-modulated signals.

Therefore, what is needed is a direct conversion transceiver that can modulate RF signals in multiple bands and multiple modes.

SUMMARY

The disclosed embodiments show novel and improved systems and methods for generating a local oscillator (LO) frequency in a direct conversion wireless communication device. In one embodiment, the system incorporates a voltage controlled oscillator (VCO), a divider, and a mixer. The divider has an input and an output produced by dividing an input signal. The divider input is operatively coupled to the VCO. The mixer has a first mixer input operatively coupled to the VCO, a second mixer input operatively coupled to the divider output, and an output. The mixer output provides the LO frequency to a phase shifter and a second divider in parallel.

In other embodiments, the system incorporates a VCO, a first divider, a second divider, and a mixer. The first divider has an input and an output produced by dividing an input signal. The input of the first divider is operatively coupled to the VCO. The second divider has an input and an output produced by dividing an input signal. The input of the second divider is operatively coupled to the output of the first divider. The mixer has a first mixer input operatively coupled to the output of the first divider, a second mixer input operatively coupled to the output of the second divider, and an output.

In another embodiment, the system incorporates a LO generator, a frequency band selection mechanism, and a configuration selection mechanism. The LO generator has one or more configurations, and includes a mixer configured to mix a VCO frequency with a divided-down version of the VCO frequency. Each configuration is associated with a frequency band of RF signals and produces an output signal whose frequency is associated with the frequency band of RF signals. The frequency band selection mechanism is configured to choose a frequency band of RF signals. The configuration selection mechanism is arranged to select a configuration associated with the chosen frequency band of RF signals.

BRIEF DESCRIPTION OF THE DRAWINGS

The features, objects, and advantages of the disclosed embodiments will become more apparent from the detailed description set forth below when taken in conjunction with the drawings in which like reference characters identify correspondingly throughout, and wherein.

DETAILED DESCRIPTION

Figure 1:
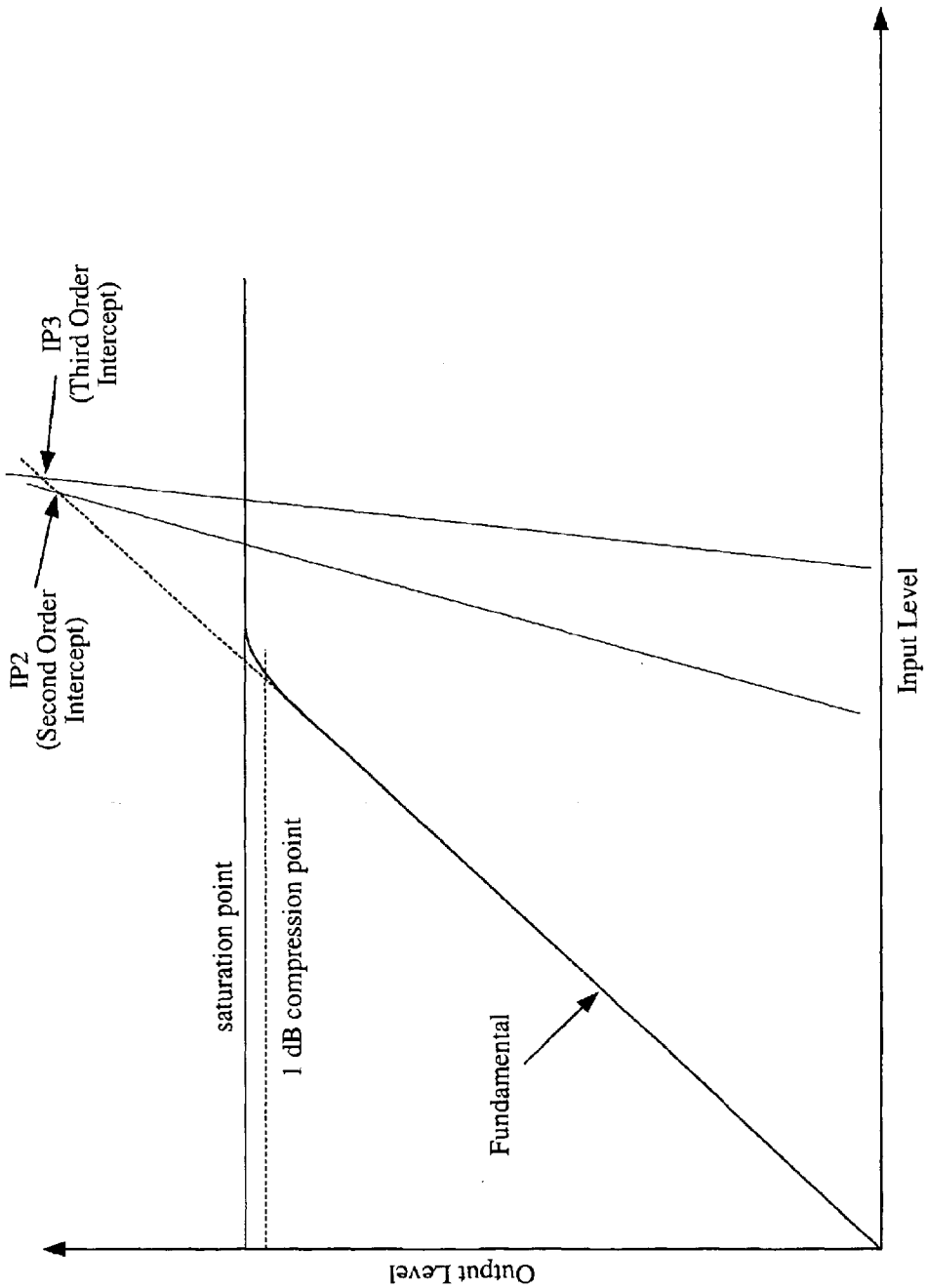
FIG. 1 is a graph plotting the saturation and compression points, and the second order and third order intercept points.
Figure 2:
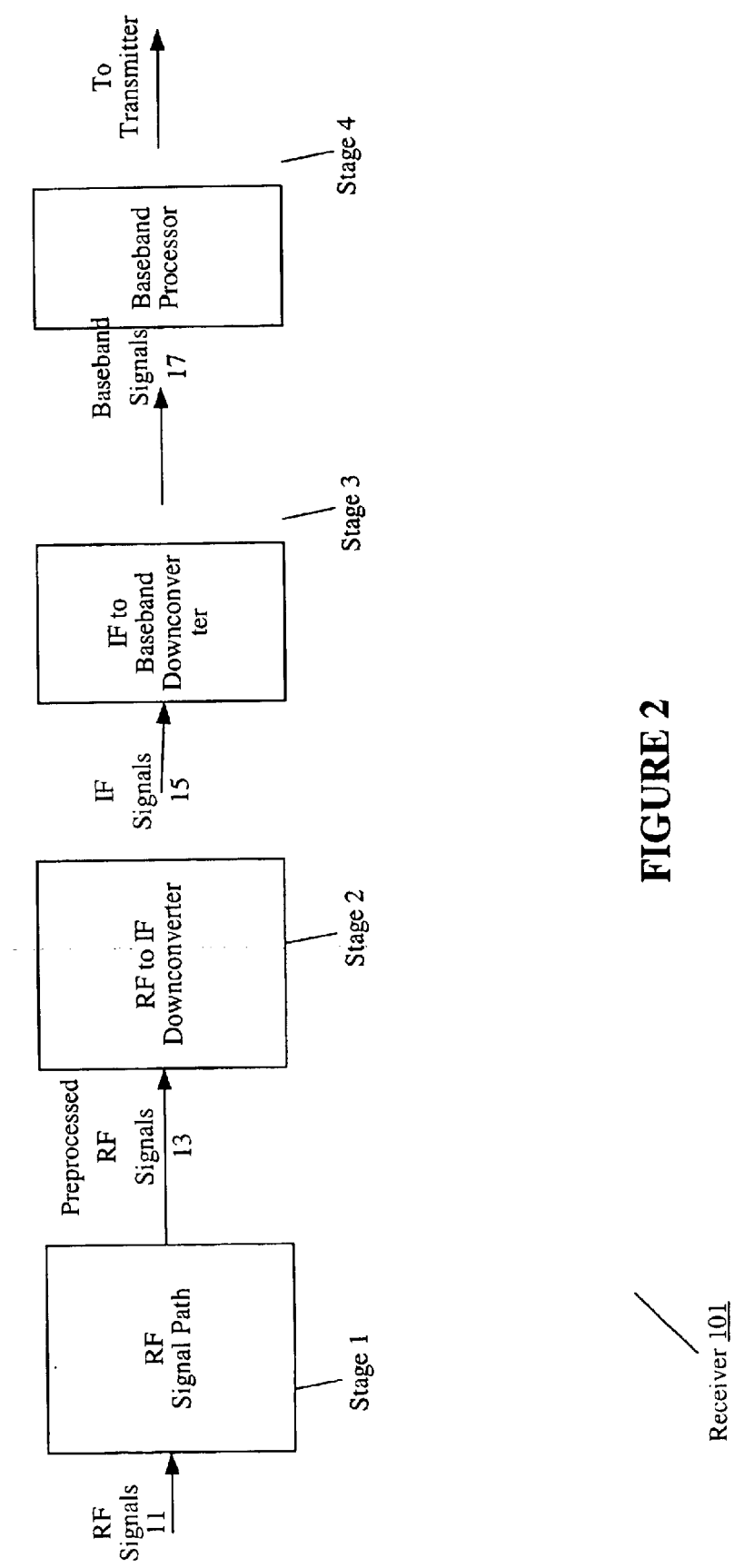
FIG. 2 is a high-level block diagram of a conventional dual conversion receiver.
Figure 3:
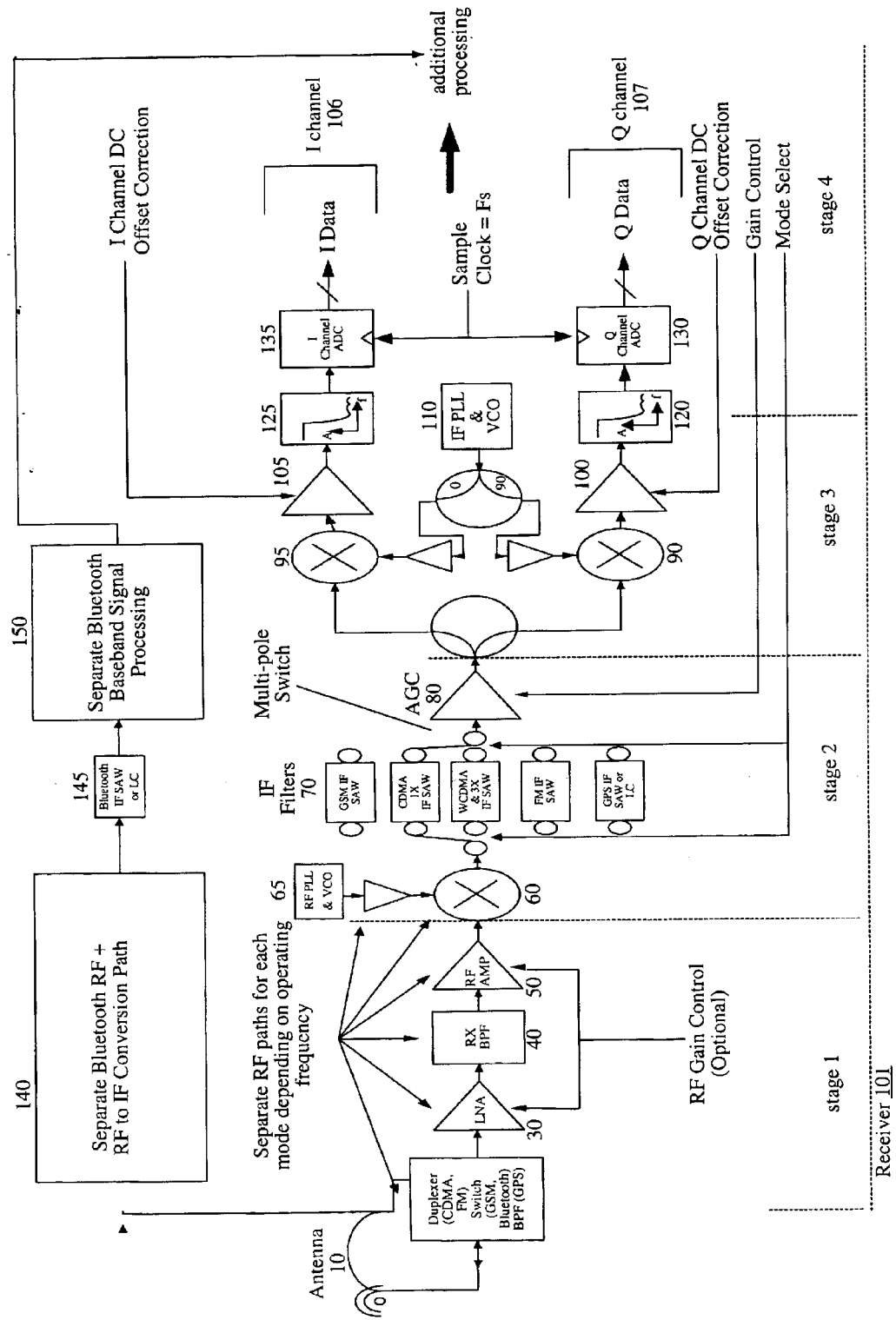
FIG. 3 is a block diagram of a conventional dual conversion receiver.
Figure 4:
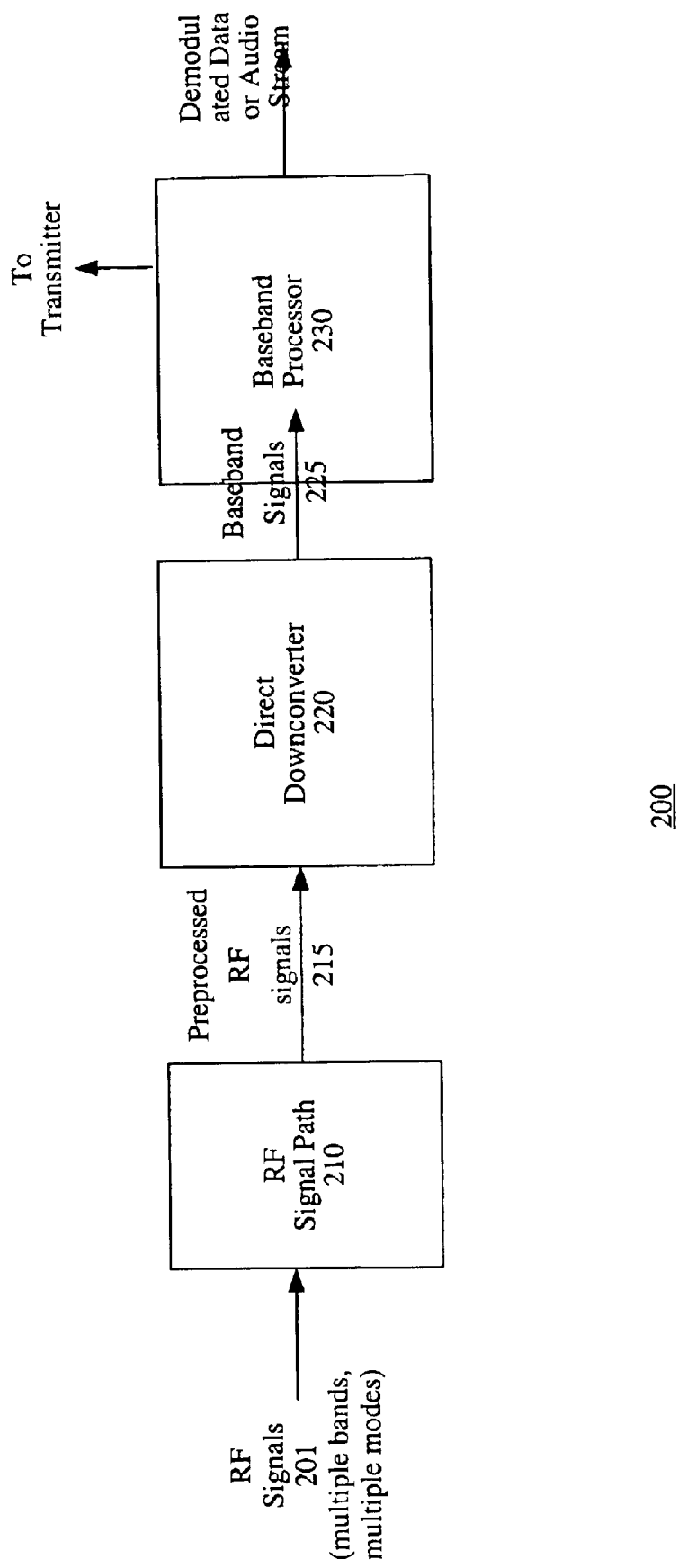
FIG. 4 is a high-level block diagram of a direct conversion receiver.

FIG. 4 is a high-level block diagram of direct downconversion receiver 200 according to an embodiment of the present invention. Receiver 200 comprises an RF signal path 210, a direct downconverter 220, and a baseband processor 230.

RF signal path 210 receives RF signals 201. RF signals 201 may comprise signals modulated in multiple modes and conveyed in multiple frequency bands. RF signal path 210 may include selection mechanisms to select among various modes and various bands. Additionally, RF signal path 210 may include amplifiers or filters to prepare RF signals 201 for further processing. Such prepared signals are designated as preprocessed RF signals 215 in FIG. 4. Direct downconverter 220 receives preprocessed RF signals 215 from RF signal path 210 and downconverts such signals to baseband signals 225.

Baseband processor 230 may perform subsequent processing on baseband signals 225, such as, for example, DC cancellation, matched and jammer filtering, sample decimation, automatic gain control, signal power measurement (received signal strength indicator, RSSI), despreading, deinterleaving, error correction, and decoding into digital data or audio streams. The processed information may then be routed to an appropriate destination, such as an output mechanism in a wireless device, which may include a display, loudspeaker, or data port. It is to be noted that baseband processor 230 may also be used by a transmitter that is complementary to receiver 200.

Figure 5:
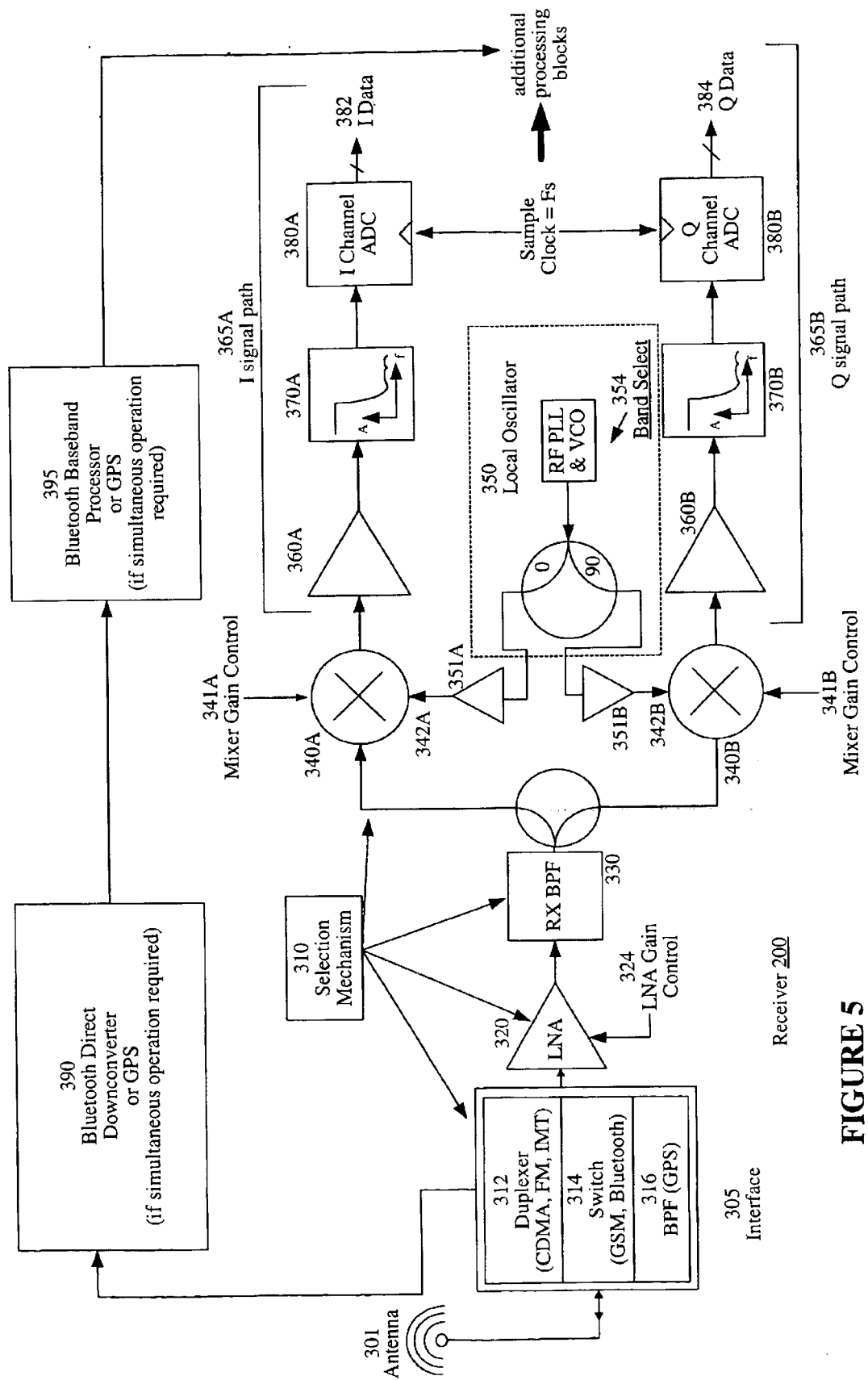
FIG. 5 is a block diagram of a direct conversion receiver.

FIG. 5 illustrates receiver 200 in more detail. An antenna 301 interfaces receiver 200 to incoming RF signals. Antenna 301 may also broadcast RF signals from a transmitter coupled to antenna 301. Multiple antennas may be used for separate operating bands or to isolate simultaneous operating modes from one another. Interface 305 may isolate received RF signals from transmitted RF signals such that receiver 200 and a transmitter may both use antenna 301.

Interface 305 may comprise one or more duplexers 312. Duplexer 312 filters signals in the incoming receive band. Additionally, duplexer 312 separates signals in the incoming receive band from signals in the outgoing transmit band. Multiple duplexers 312 may be employed if multiple bands of operation are required by a particular receiver or transceiver application. As shown in FIG. 5, one duplexer 312 may process signals modulated in the CDMA, FM, and IMT modes, assuming that the associated operating bands all fit within a band of duplexer 312.

Interface 305 may also comprise one or more switches 314 and bandpass filters 316. Switch 314 selects between receive and transmit operations. For instance, switch 314 may correspond to the GSM or Bluetooth modes, in which signals are not received and transmitted simultaneously. Bandpass filter 316 filters GPS signals in the incoming receive band. Because GPS signals are received, and not transmitted, a duplexer need not be employed. Other bandpass filters 316 may be included in receiver 200 for other analogous receive-only modes.

A low noise amplifier (LNA) 320 is coupled to interface 305 and amplifies received RF signals. LNA 320 may be chosen to provide a minimal noise figure in the receive band, but a sufficiently high gain to minimize noise figure contributions from subsequent stages in receiver 200. The gain of LNA 320 may be controlled via an LNA gain control 324. Transmit power may leak into receiver 200 from interface 305. For instance, duplexer 312 may not entirely filter the transmit power. Thus, LNA 320 may require a high compression and third order intercept point.

LNA 320 is coupled to a RX bandpass filter (BPF) 330. BPF 330 further rejects transmitter signals that fall outside of the receive band. It is to be noted that BPF 330 may not be necessary in some embodiments of the present invention. For instance, as noted earlier, signals modulated in the GSM mode may not be received and transmitted simultaneously if maximum data rates in GPRS (General Packet Radio Service) are not supported.

FIG. 5 depicts one RF signal path including one duplexer 312, one LNA 320 and one BPF 330. However, multiple RF signal paths may be included in receiver 200. Each signal path may correspond to one or more particular operating frequency bands of receiver 200. For instance, receiver 200 may include respective Cellular, PCS, IMT, and GSM signal paths. Each RF path may include, as needed, a duplexer, switch, and/or bandpass filter, a LNA, a BPF, and I and Q mixers. Additionally, simultaneous GPS reception while operating with other modes may require separate LO generation, baseband amplifiers, analog low-pass filters, analog-to-digital converters, I/Q digital processing, and demodulation.

Selection mechanism 310 switches among different RF signal paths depending on operating frequency bands active at a given time. Selection mechanism 310 may comprise a band select device coupled to, for example, various duplexers and BPFs. Selection mechanism 310 may also be coupled to I and Q channel mixers 340A, 340B. For instance, for received signals in the US Cellular band, selection mechanism 310 may switch to a duplexer 312, a LNA 320, and a BPF 330 that together appropriately filter and amplify the received signals.

The output of BFP 330 is coupled to an input of I and Q channel mixers 340A, 340B. In an exemplary implementation, BPF 330 may have a differential output (not shown) to connect to differential inputs (not shown) of mixers 340A, 340B. Accordingly, the positive and negative output terminals of BPF 330 may be coupled to the positive and negative input terminals of mixer 340A, and to the positive and negative input terminals of mixer 340B. Such a differential signal path arrangement reduces LO and TX coupling into the RF signal path and increases common mode rejection of amplitude-modulated jammers (higher second order input intercept level at the mixer inputs). Thus, isolation and jammer rejection in receiver 200 is improved.

Alternatively, a transformer may be coupled to a single-ended output of BPF 330. The transformer may convert the single-ended signal to a differential signal, which may be coupled to differential inputs of mixers 340A, 340B.

As shown in FIG. 5, a local oscillator (LO) 350 is coupled to buffer amplifiers 351A, 351B. Buffer amplifiers 351A, 351B are coupled to a second input 342A of mixer 340A and a second input 342B of mixer 340B, respectively. Buffer amplifiers 351A, 351B may have differential outputs if I and Q mixers 340A, 340B have differential inputs. In some embodiments, buffer amplifiers need not be included in the design of receiver 200.

LO 350 may comprise a frequency generator that may generate output signals at various frequencies. For instance, LO 350 may output a first signal and a second signal that is phase-shifted from the first signal by $90°$. LO 350 may include a phase-locked loop (PLL), a voltage controlled oscillator (VCO), a frequency mixing mechanism, and a phase shifting mechanism. LO 350 may include a band select 354 that controls LO 350 depending on an operating frequency of received RF signals. In an exemplary embodiment, LO 350 uses differential paths to mitigate LO leakage and noise coupling to and from the signal paths at the I and Q mixer RF ports.

Each mixer 340A, 340B mixes a received RF signal from BPF 330 with a signal received from LO 350 at the second input 342A, 342B of mixers 340A, 340B. The mixing process multiplies the signals together. Thus, mixers 340A, 340B directly downconvert received RF signals to I and Q baseband signals. In an exemplary implementation, mixers 340A, 340B have associated gain that may be adjusted via mixer gain control 341A, 341B.

After downconversion, the I and Q signals are processed along respective signal paths 365A, 365B. The I signal path 365A is representative of both signal paths, and may include an amplifier 360A, an anti-aliasing filter 370A, and an I channel analog-to-digital converter (ADC) 380A. Amplifier 360A is coupled to the output of mixer 340A. After processing and analog-to-digital conversion along the respective signal paths, digital I channel data 382 and channel data 384 may be further processed. In some embodiments, the I and Q signals may be processed along operating mode-specific paths. In other embodiments, I and Q signal paths may be shared among modes.

Receiver 200 may contain Bluetooth-specific modules. Bluetooth direct downconverter 390 and Bluetooth baseband processor 395, as shown in FIG. 5, may be functionally and structurally similar to the structures described above. However, because Bluetooth may operate concurrently with other operating modes, such as CDMA, Bluetooth direct downconverter 390 and baseband processor 395 may be implemented as Bluetooth-dedicated modules. Similarly, GPS may operate concurrently and require a separate baseband signal path and LO generation circuitry.

Figure 6:
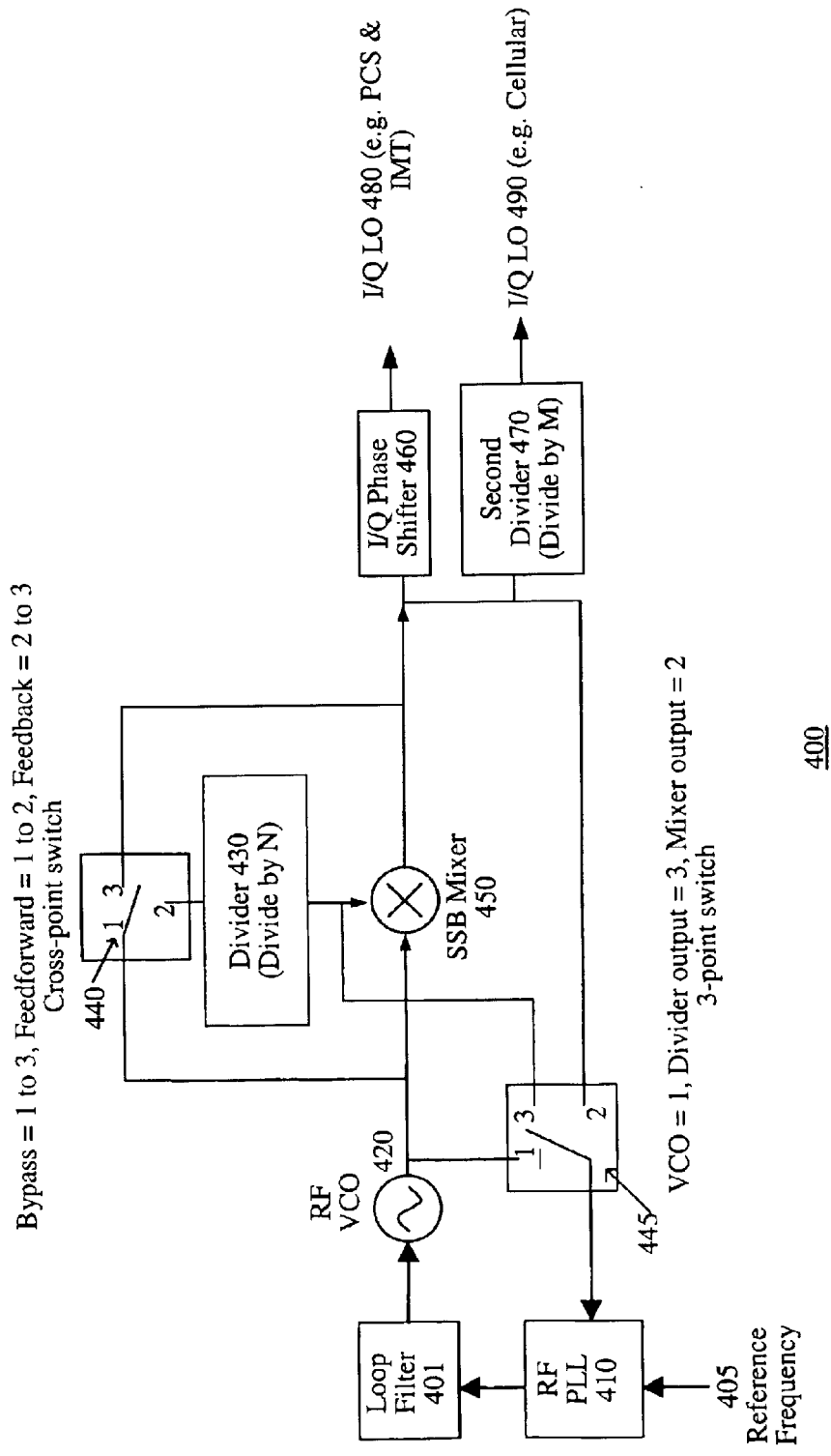
FIG. 6 is a block diagram of a system for generating a local oscillator frequency according to an embodiment of the present invention.

FIG. 6 illustrates system 400 for generating a local oscillator frequency according to an embodiment of the present invention. It is to be noted that system 400 may be incorporated into wireless receivers, transmitters, or transceivers. For instance, system 400 may be incorporated into receiver 200 as LO 350 in FIG. 5. System 400 comprises a phase-locked loop (PLL) 410, a loop filter 401, a mixer 450, a voltage controlled oscillator (VCO) 420, and a switch 440.

Switch 440 may be configured to have multiple positions. In FIG. 6, switch 440 is a cross-point switch having three positions. In a first position (1-2), described herein as "Feedforward," switch 440 couples VCO 420 to the input of a divider 430. In a second position (2-3), "Feedback," switch 440 couples the output of mixer 450 to the input of divider 430. In a third position (1-3), "Bypass," switch 440 couples VCO 420 to the output of mixer 450 and the second input of mixer 450 is disabled. Although system 400 is shown to contain a switch, in other embodiments, system 400 need not contain a switch. For instance, VCO 420 may be directly coupled to divider 430. The position of switch 440 may be controlled by a control mechanism (not shown), such as a band select, depending on the frequency band of received RF signals.

VCO 420 may comprise a single-ended output VCO that is external to a chip that includes the associated receiver, transmitter, or transceiver. An external VCO may have better phase noise than a VCO integrated within an ASIC (application-specific integrated circuit). However, an integrated VCO may be sufficient depending on the jamming requirements inherent in a given operating band. For an external VCO 420, PLL 410 may be directly coupled to VCO 420. Additionally, PLL 410 may be coupled to the output of mixer 450 if PLL 410 is integrated within system 400. PLL 410 receives a signal at a reference frequency 405 to create discrete channel spacings within each operating band.

The embodiment shown in FIG. 6 includes a PLL input switch 445. Switch 445 may couple PLL 410 to VCO 420, to the output of mixer 450, or to the output of divider 430. As is well known in the art, PLL 410, loop filter 401, and VCO 420 cooperate together to output a signal having a VCO frequency. The VCO frequency may be above or below the frequency of received or transmitted signals. Divider 430 may comprise a frequency divider that outputs a signal whose frequency is a divided-down version of an input signal. For instance, divider 430 may divide by an integer N, wherein the value of N may be set by a control signal.

VCO 420 is coupled to a first input of mixer 450. Based on the position of switch 440, as described above, a second input of mixer 450 may be coupled, through divider 430, to VCO 420 (Feedforward), the output of mixer 450 (Feedback), or an open circuit (Bypass). Mixer 450 may comprise a Single Side Band (SSB) mixer, or image reject mixer, that outputs only one primary mixer product. An SSB mixer minimizes unwanted mixer products at the mixer output. Specifically, a SSB mixer provides a frequency output that is either the sum of the two input frequencies (the upper sideband, or USB) or the difference of the two input frequencies (the lower sideband, or LSB). An upper SSB mixer retains the upper sideband and cancels the lower SSB. Conversely, a lower SSB mixer retains the lower sideband and cancels the upper sideband. Mixer 450 may be configured to operate between USB and LSB modes depending on a control signal coupled to mixer 450.

System 400 may also include a second divider 470 to create quadrature LO signals 490. Second divider 470 may divide down an input frequency by an integer M, and may consist of flip-flops. When divider 470 consists of two flip-flops, the first flip-flop may clock off the rising edge of the input signal, while the second flip-flop clocks off the falling edge. The respective outputs of the flip-flops may be 90° out of phase. As such, each flip-flop may differentially drive either of the I and Q mixers 340A, 340B. In other embodiments, buffer amplifiers 351A, 351B may be placed between second divider 470 and I and Q mixers 340A, 340B. When M=2, that is, second divider 470 divides by 2, second divider 470 functions as a broadband phase shifter having utility, when used in conjunction with divider 430, for a wide range of frequencies. Second divider 470 may generate I and Q mixer LO signals for US and Japan Cellular bands.

Phase shifter 460 may be included in system 400 in parallel with second divider 470. Alternatively, system 400 may only include phase shifter 460. Phase shifter 460, which may comprise an LCR network or active elements, may be coupled to the output of mixer 450. Phase shifter 460 may receive an input signal and produce quadrature LO output signals 480. In the case of a receiver, each quadrature signal may be mixed with received RF signals to downconvert the RF signals to I and Q baseband components. In an exemplary embodiment, phase shifter 460 is operative for the higher operating bands of PCS (US or Korean) and IMT.

According to an embodiment of the present invention, the value of N for divider 430, the position of switch 440, and the mode of mixer 450 may be varied to generate a wide range of LO frequencies. In addition, the value of M for second divider 470 may be varied. Although a wide range of LO frequencies may be generated, VCO 420 need only operate in a relatively narrow tuning range. Accordingly, system 400 may be implemented in a wireless multi-band and multi-mode receiver, transmitter, or transceiver.

In exemplary implementations, system 400 includes differential signal paths. For instance, the output of VCO 420, and the inputs and outputs of mixer 450 and divider 430 may be differential. As such, radiated I and Q LO energy and conducted coupling to the RF signal path in the wireless device incorporating system 400 may be minimized.

A microprocessor (not shown) in a wireless device including system 400 may determine an applicable frequency band for RF signals. Based on the chosen band, a configuration selection mechanism, such as band select 354 in FIG. 5, may select a configuration in system 400 that is associated with the chosen frequency band. As such, appropriate control signals to set the value of N for divider 430, the position of switch 440, the mode of mixer 450, and the value of M for second divider 470 may be generated in system 400.

Table 1 sets forth exemplary configurations for system 400 when implemented in a receiver context. VCO 420 is controlled to operate from about 1600 to 1788 MHz. VCO 420 may be a primary source of radiated and conducted noise in a wireless device. As Table 1 illustrates, the VCO frequency ranges are distinct from the associated RF receive frequency ranges. Thus, the below configurations minimize the effects of VCO noise in a wireless device.

Consistent with the present invention, other configurations may be prepared to optimize the tuning range and center frequency of VCO 420 for different receive frequency ranges and for different design techniques, such as external VO or integrated VCO implementations. Additional dividers may be included in system 400 to provide for such configurations.

Divider 430 and mixer 450 may produce undesired LO spurs that fall outside of a desired receive band. However, the output of mixer 450 will suppress such spurs. Further, ports 342A, 342B of I and Q mixers 340A, 340B (see FIG. 5) may include resonators, which may also suppress such spurs. RF signal paths may also have multiple RF BPF responses, which may reject jamming products at the same frequencies as the LO spurs.

As discussed, second and divider 460 may create quadrature LO signals 480. The I and Q mixers 340A, 340B receive the quadrature LO signals 480, which may be passed by buffers 351A, 351B, as inputs. As such, phase variations in the load resistance and capacitance of I and Q mixers 340A, 340B may give rise to systemic errors. However, phase matching requirements may be met by implementing I and Q mixers 340A, 340B on the same chip. Thus, residual sideband specifications for a receiver may be met.

Amplitude matching between the I and Q channels may be necessary. Exemplary amplitude matching approaches include calibrating the I and Q channel gain through analog or digital gain compensation. To achieve analog gain compensation (not shown), an independent or switchable power detection mechanism may be coupled to each of the I and Q channels to measure the received signal strength indicator (RSSI) of the channels and offset the gain accordingly. An ASIC may store calibration values for the I and Q channels. Via a digital bus interface between the ASIC and the power detection mechanism, calibration values may be looked up, and the gain may be compensated. To achieve digital gain compensation (not shown), the baseband path may include a digital multiplier after the ADC that multiplies the I and Q signals together. Thus, calibration values stored in an ASIC may be looked up, and the I and Q channel gain may be compensated accordingly.

In another embodiment (not shown), a GPS-specific signal path may be included in a wireless receiver or transceiver. GPS-modulated signals are received in only one frequency. Therefore, a receiver need only tune to one GPS frequency. In particular, the GPS-specific path may have a PLL and VCO exclusively for GPS signals. The VCO, which may be on-chip or off-chip, may operate at 3150.84 MHz, or twice the GPS frequency. The GPS VCO may then be

TABLE 1

LO Control Configurations for Multi-Band Direct Downconversion Receiver

| RF Frequency Band | RF Receive Frequency Range (MHz) | Divider Value N | SSB Mixer | Switch Position/ Second Divider Value M | RX VCO Frequency Range (MHz) |
|---|---|---|---|---|---|
| US PCS | 1930 to 1990 | 8 | USB | Feedforward | 1716 to 1769 |
| US Cellular | 869 to 894 | disabled | disabled | Bypass & Divide by 2 | 1738 to 1788 |
| Japan Cellular | 832 to 870 | disabled | disabled | Bypass & Divide by 2 | 1664 to 1740 |
| IMT | 2110 to 2170 | 4 | USB | Feedforward | 1688 to 1736 |
| Korean PCS | 1840 to 1875 | 8 | USB | Feedforward | 1635 to 1651 | coupled to, and divided down by, a divider (dividing by 2) to generate a LO frequency for direct downconversion of GPS RF signals. Although a separate GPS RF signal path may be provided in a receiver, the GPS baseband path may be separate or shared with signals modulated according to other modulation standards. When separate, baseband processing of GPS signals may occur concurrently with baseband processing of other modulated signals. When shared, savings in current and board area may be achieved.

Because Bluetooth may operate concurrently with other operating modes, such as CDMA, a separate VCO and LO generator may be included in a receiver or transceiver to assist in generating a LO frequency for direct downconversion of Bluetooth signals.

Figure 7:
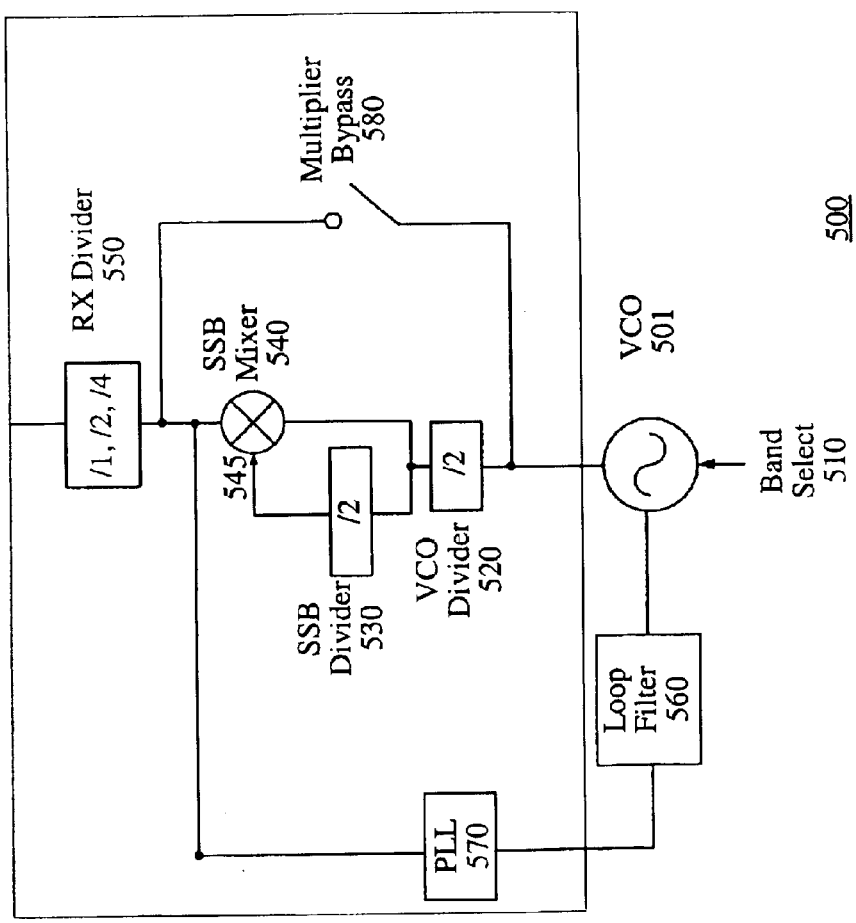
FIG. 7 is a block diagram of a system for generating a local oscillator frequency according to an embodiment of the present invention.

FIG. 7 illustrates an alternative system 500 for generating a local oscillator frequency. System 500 comprises a PLL 570, a loop filter 560, a multi-band VCO 501, a VCO divider 520, a SSB mixer 540, a SSB divider 530, and a RX divider 550. Multi-band VCO 501, PLL 570, and loop filter 560 cooperate together to output a VCO frequency in variable frequency ranges. Band select 510 determines an applicable frequency range for multi-band VCO 501.

VCO divider 520 is coupled to multi-band VCO 501. VCO divider 520 may divide down the VCO frequency by an integer P, such as 2. The divided-down output of VCO divider 520 is coupled to the input of SSB divider 530. SSB divider 530 may divide down the output frequency of VCO divider 520 by an integer, such as 2. The output of SSB divider 530 and the output of VCO divider 520 are coupled to respective inputs of SSB mixer 540. SSB mixer 540 mixes the signals together. Depending on whether SSB mixer 540 is operating as an USB mixer or a LSB mixer, the sum or difference of the input signals is outputted by mixer 540. Therefore, VCO divider 520, SSB divider 530, and SSB mixer 540 act in concert as a fractional frequency multiplier. The output of mixer 540 is coupled to the input of RX divider 550. RX divider 550 may divide down the input signal by an integer, such as 1 or 2.

By varying the frequency band of multi-band VCO 501, as well as the mode of SSB mixer 540, and the divider values of VCO divider 520, SSB divider 530, and RX divider 550, a wide range of LO frequencies may be generated by system 500. Table 2 illustrates exemplary configurations for system 500 that make system 500 suitable for implementation in a multi-band wireless receiver.

frequency. Specifically, to generate Cellular I and Q mixer LO signals, VCO 501 may be run at 4 times the receive frequency, and RX divider 550 may divide by 4. However, tuning may be more problematic due to the wide operating range of multi-band VCO 501. It is to be appreciated that system 500 may directly couple multi-band VCO 501 to RX divider 550, and that multiplier bypass switch 580, SSB divider 530, SSB mixer 540, and VCO divider 520 may be eliminated from system 500.

Additionally, system 500 may include a switch (not shown) coupled to multi-band VCO 501 and input 545 of SSB mixer 540. When the switch is closed, SSB mixer 540 may mix the VCO frequency with a divided-down version of the VCO frequency. As such, system 500 may generate I and Q mixer LO signals in a similar manner to that employed in system 400 above.

Figure 8:
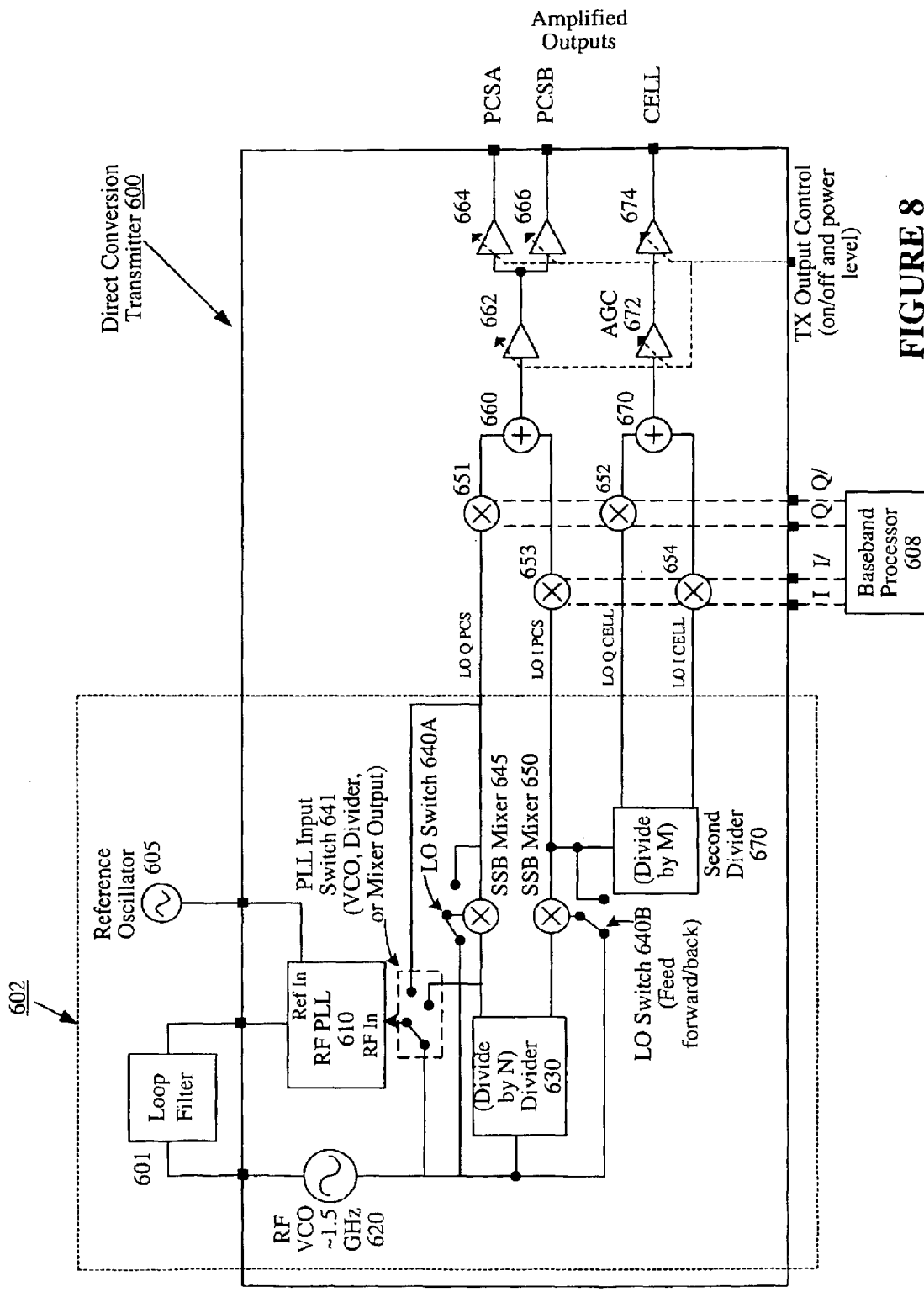
FIG. 8 illustrates an embodiment of a zero IF transmitter.

FIG. 8 illustrates an embodiment of a direct upconversion, or zero IF, transmitter 600. Transmitter 600 includes system 602, which generates a local oscillator frequency. System 602 is similar to system 400 above, but is specifically constructed and operative in a wireless direct upconversion transmitter. System 602 comprises a PLL 610, a loop filter 601, first and second SSB mixers 645, 650, a VCO 620, a PLL input switch 641, LO switches 640A and 640B, and a second divider 670.

The phase noise requirements for a transmitter are less demanding than those for a receiver, which must meet jamming requirements. Therefore, VCO 620 may be more readily integrated on a transmitter or transceiver ASIC. In other embodiments, however, VCO 620 may be implemented off-chip. VCO 620, loop filter 601, PLL 610, and reference oscillator 605 cooperate together to produce a VCO output frequency. PLL input switch 641 may selectively couple PLL 610 to VCO 620, to an output of divider 630, or to the output of first SSB mixer 645. As such, the input source for PLL 610 may be switched from VCO 620 to either a signal at the output of divider 630 or a signal at the output of first SSB mixer 645. Thus, when a desired RF frequency is generated, locking to that frequency may occur.

Switches 640A, 640B each have two positions. Additional positions are possible in other embodiments. In other implementations, switches 640A, 640B need not be included. In the Feedforward position of switch 640A, switch 640A couples VCO 620 to an input of first SSB mixer 645. In the Feedback position, switch 640A couples the

TABLE 2

LO Control Configurations for Multi-Band Direct Downconversion Receiver

| RF Frequency Band | RF Receive Frequency Range (MHz) | VCO Divider Value | SSB Divider Value | SSB Mixer | RX Divider Value | RX VCO Frequency Range (MHz) |
|---|---|---|---|---|---|---|
| US PCS | 1930 to 1990 | 2 | 2 | USB | 1 | 2573 to 2653 |
| US Cellular | 869 to 894 | 2 | 2 | USB | 2 | 2317 to 2384 |
| Japan Cellular | 832 to 870 | 2 | 2 | USB | 2 | 2219 to 2320 |
| IMT | 2110 to 2170 | 2 | 2 | USB | 1 | 2813 to 2893 |
| Korean PCS | 1840 to 1875 | 2 | 2 | USB | 1 | 2453 to 2500 |

Other configurations are possible in system 500. For instance, system 500 may include a multiplier bypass switch 580 coupled to multi-band VCO 501 and RX divider 550. When the switch is closed, multi-band VCO 501 may be run at 2 times, or 4 times, the operating frequency of received signals. RX divider 550 may then respectively divide the VCO output frequency by 2 or 4 to generate the desired LO output of SSB mixer 645 to the LO port of SSB mixer 645. In the Feedforward position of switch 640B, switch 640B couples VCO 620 to an input of second SSB mixer 650. In the Feedback position, switch 640B couples the output of SSB mixer 650 to the LO port of SSB mixer 650.

VCO 620 is coupled to an input of divider 630. Divider 630 divides down the VCO output frequency by an integer N. Divider 630 produces a first and a second output signal. The first output of divider 630 is coupled to first SSB mixer 645. The second output of divider 630 is coupled to second SSB mixer 650. The signals at the first and second divider outputs are both divided-down versions of the input frequency, but differ in phase by 90°.

When switch 640A is in the Feed Forward position, first SSB mixer 645 mixes the VCO output frequency with the first divided-down version outputted by divider 630. Similarly, second SSB mixer 650 mixes the VCO output frequency with the second divided-down version outputted by divider 630. The outputs of first and second SSB mixers 645, 650 are identical in frequency and differ in phase by 90°. The outputs of first and second SSB mixers 645,650 are transmitter LO frequencies of system 602.

The output of second SSB mixer 650 is coupled to second divider 670. Second divider 670 may divide down an input frequency by an integer M. Second divider 670 produces a first and a second output signal. The first and second output signals are in quadrature. The outputs of second divider 670 are transmitter LO frequencies of system 602.

By varying the values of N and M, the mode of SSB mixers 645, 650, and the positions of switches 640A, 640B, system 602 may generate a wide range of transmitter LO frequencies. Thus, system 602 is appropriate for implementation in direct upconversion transmitters such as transmitter 600. Table 3 lists exemplary configurations associated with transmitter operating bands. Additional configurations may be prepared that are consistent with the teachings of the present invention. As described above, a desired frequency band may be chosen via a frequency band selection mechanism, and an associated configuration may be selected via a configuration selection mechanism.

TABLE 4-continued

TX Offset Relative to RX Channel Frequency

| Mode | TX Offset (MHz) |
|---|---|
| Korean PCS | −90 |
| US PCS | −80 |
| US Cellular | −45 |

Specifically, LO generation circuitry of system 602 (PLL 610, loop filter 601, first and second SSB mixers 645, 650, VCO 620, and switches 640A, 640B) may generate a receive LO frequency. A second oscillator, which is a fixed offset LO, may be coupled to an input of each of the first and second SSB mixers 645, 650. Accordingly, first SSB mixer 645 and second SSB mixer 650 may mix the receive LO frequency with the offset LO to produce the transmit LO frequency. However, it is to be appreciated that the received LO may generate spurious outputs. Thus, off-chip filtering within a transmitter or transceiver may be required to meet the conducted spurious leakage specification for the receive band. Such filtering may reject the spur product at the receive frequency.

Transmitter 600 may employ the LO frequency generated by system 602 to transmit RF signals. Baseband processor 608 may be external to transmitter 600, as shown in FIG. 8, or integrated within a transceiver comprising transmitter 600. Baseband processor 608 provides a pair of output signals. Each output signal may be implemented as a balanced or differential pair. The two outputs represent the I and

TABLE 3

LO Control Configurations for Multi-Band Direct Upconversion Receiver

| RF Frequency Band | RF Transmit Frequency Range (MHz) | Divider Value N | SSB Mixer | Switch Position/ Second Divider Value M | TX VCO Frequency Range (MHz) |
|---|---|---|---|---|---|
| US PCS | 1850 to 1910 | 4 | USB | Feedforward | 1480 to 1528 |
| US Cellular | 824 to 849 | 8 | USB | Feedforward & Divide by 2 | 1465 to 1509 |
| Japan Cellular | 887 to 925 | 4 | USB | Feedforward & Divide by 2 | 1419 to 1480 |
| IMT | 1920 to 1980 | 4 | USB | Feedforward | 1536 to 1584 |
| Korean PCS | 1750 to 1775 | 4 | USB | Feedforward | 1400 to 1424 |

In another embodiment (not shown), system 602 may generate a transmit LO frequency by mixing the receive LO frequency for a receiver with a fixed offset LO frequency. This approach recognizes that the following modulation standards have a fixed frequency offset between TX and RX channels, as shown in Table 4.

TABLE 4

TX Offset Relative to RX Channel Frequency

| Mode | TX Offset (MHz) |
|---|---|
| GSM | −45 |
| IMT | −190 |
| Japan Cellular | +55 |

Q baseband analog signals for each mode, and are provided as separate signal paths so that quadrature modulation of the signals may be performed in later stages of transmitter 600.

In an exemplary implementation, transmitter 600 includes three RF outputs. Two of the outputs may correspond to PCS or IMT signal bands PCSA and PCSB, and the other may correspond to Cellular bands CELL. For the PCS RF outputs, a first RF mixer 651 is coupled to SSB mixer 645 and a first baseband output of baseband processor 608. First RF mixer 651 upconverts the baseband signal directly to the desired RF frequency. A second RF mixer 653 is coupled to SSB mixer 650 and a second baseband output of baseband processor 608. Second RF mixer 653 upconverts the baseband signal directly to the same RF frequency as at the output of first RF mixer 651. The outputs of first and second RF mixers 651, 653 are in quadrature due to the relative phase difference of the LO signals used to upconvert the baseband signals.

The quadrature RF signals are then coupled to a signal summer 660 that combines the two quadrature signals into a single signal. The inputs of signal summer 660 may be balanced to correspond to the balanced outputs from each of first and second RF mixers 651, 653. The output of signal summer 660 may also be a balanced signal to minimize signal interference from common mode noise sources.

The output of signal summer 620 may be simultaneously coupled to two amplifier chains. Both amplifier chains may be configured to operate in the PCS transmit band. As shown in FIG. 8, a first amplifier chain may include AGC amplifiers 662 and 664. A second amplifier chain may include AGC amplifiers 662 and 666.

For the Cellular RF output, a third RF mixer 652 is coupled to the first output of second divider 670 and a first baseband output of baseband processor 608. Third RF mixer 652 upconverts the baseband signal directly to the desired RF frequency. A fourth RF mixer 654 is coupled to the second output of second divider 670 and a second baseband output of baseband processor 608. Fourth RF mixer 654 upconverts the baseband signal directly to the same RF frequency as at the output of third RF mixer 652. The outputs of third and fourth RF mixers 652, 654 are in quadrature due to the relative phase difference of the LO signals used to upconvert the baseband signals.

The quadrature RF signals are then coupled to a signal summer 670 that combines the two quadrature signals into a single signal. The inputs of signal summer 670 may be balanced to correspond to the balanced outputs from each of third and fourth RF mixers 652, 654. The output of signal summer 670 may also be a balanced signal to minimize signal interference from common mode noise sources.

The output of signal summer 670 may be coupled to a third amplifier chain. The third amplifier chain may be configured to operate in the Cellular transmit band. As shown in FIG. 8, the third amplifier chain may include AGC amplifiers 672 and 674.

Transmitter 600 may be configured such that only one amplifier chain is operational at any time. As such, when transmitter 600 is configured to transmit in a particular frequency band, only the amplifier chain supporting that frequency band may be operational. The idle amplifier chain may be powered down by control circuits (not shown) in order to conserve power. It is to be appreciated that the three amplifier chains shown in FIG. 8, and other such amplifier chains, may also include, or be coupled with, transmit filters, isolators, or diplexers according to methods well known in the art.

The foregoing detailed description refers to the accompanying drawings that illustrate exemplary embodiments of the present inventions. Other embodiments are possible and modifications may be made to the embodiments without departing from the spirit and scope of the invention. For instance, many of the above devices may be indirectly coupled to one another such that the devices are separated by intermediate devices, such as filters or amplifiers. Moreover, the teachings of the present invention may be applied to future-developed modulation standards and operating bands. Therefore, the detailed description is not meant to limit the invention. Rather, the scope of the invention is defined by the appended claims.

What is claimed:

1. A method of generating a local oscillator (LO) frequency in a multi-band direct conversion wireless communication device, the method comprising:

receiving a signal, from voltage controlled oscillator (VCO), having a VCO frequency;

dividing the VCO frequency by a number N to produce a signal having a divided-down frequency; and mixing the signal having the VCO frequency with the signal having the divided-down frequency to produce an output signal having the LO frequency.

2. The method of claim 1, further comprising dividing the LO frequency by a number M.

3. The method of claim 1, further comprising shifting the phase of the output signal.

4. The method of claim 1, wherein the device includes a receiver.

5. The method of claim 4, further comprising mixing the output signal with a signal having an offset frequency to produce an LO frequency for a transmitter.

6. The method of claim 1, wherein the device includes a transmitter.

7. A method of generating a local oscillator (LO) frequency in a multi-band direct conversion wireless communication device, the method comprising:

receiving a signal, from a voltage controlled oscillator (VCO), having a VCO frequency;

dividing the VCO frequency by a number N to produce a signal having a divided-down frequency;

dividing the divided-down frequency by a number M to produce a second signal having a further divided-down frequency; and mixing the signal having the VCO frequency with the second signal having the further divided-down frequency to produce an output signal having the LO frequency.

8. The method of claim 7, further comprising dividing down the LO frequency by a number P.

9. The method of claim 7, wherein the VCO is a multi-band VCO.

10. A method of generating a local oscillator (LO) frequency in a multi-band direct conversion wireless communication device, the method comprising:

configuring an LO generator to have one or more configurations, each configuration being associated with at least one frequency band of RF signals and producing an output signal whose frequency is associated with the at least one frequency band of RF signals, and to mix a VCO frequency with a divided-down version of the VCO frequency;

choosing a frequency band of RF signals; and selecting a configuration associated with the chosen frequency band of RF signals.

11. The method of claim 10, further comprising controlling the LO generator based on the selecting.

12. A system for generating a local oscillator (LO) frequency in a multi-band direct conversion wireless communication device, the system comprising:

a voltage controlled oscillator (VCO);

a divider having an input and an output produced by dividing an input signal, the divider input being operatively coupled to the VCO; and a mixer having a first mixer input operatively coupled to the VCO, a second mixer input operatively coupled to the divider output, and an output providing the LO frequency.

13. The system of claim 12, wherein the VCO is external to a chip that includes the device.

14. The system of claim 13, wherein the VCO has a single-ended output.

15. The system of claim 12, wherein the VCO is integrated in a chip that includes the device.

16. The system of claim 12, wherein the VCO operates below a frequency of RF signals.

17. The system of claim 12, wherein the VCO operates above a frequency of RF signals.

18. The system of claim 12, wherein the VCO operates at frequencies between 1600 and 1788 MHz.

19. The system of claim 12, wherein the VCO is operatively coupled to a phase-locked loop (PLL) further comprising a second PLL and a second VCO for signals received when in a GPS mode, the second VCO operating at two times the frequency of received GPS signals.

20. The system of claim 12, further comprising a third PLL and a third VCO for signals received when in a Bluetooth mode.

21. The system of claim 12, wherein the mixer includes a single side band (SSB) mixer.

22. The system of claim 21, wherein the SSB mixer is a low side SSB mixer.

23. The system of claim 21, wherein the SSB mixer is a high side SSB mixer.

24. The system of claim 12, wherein the mixer output is operatively coupled to a phase-locked loop (PLL), wherein the PLL is internal to a chip that includes the device.

25. The system of claim 12, wherein the divider input is selectively coupled to the VCO.

26. The system of claim 25, wherein a switch selectively couples the divider input to the VCO.

27. The system of claim 26, wherein the switch is controlled by a switch control based on a band of the RF signals.

28. The system of claim 12, wherein the divider input is selectively coupled to the mixer output.

29. The system of claim 12, wherein the mixer output is selectively coupled to the VCO.

30. The system of claim 12, further comprising a phase shifter having an input coupled to the mixer output, the phase shifter having an output that produces quadrature signals.

31. The system of claim 30, wherein the phase shifter comprises an active phase shifter.

32. The system of claim 12, further comprising a second divider having an input operatively coupled to the mixer output and an output produced by dividing an input signal.

33. The system of claim 32, wherein the second divider divides by 2.

34. The system of claim 32, wherein the second divider outputs a first signal and a second signal, the first signal being 90 degrees out of phase of the second signal.

35. The system of claim 34, wherein the first signal drives one of an I and Q mixer in the device.

36. The system of claim 12, wherein
the device includes a receiver, wherein
a band of received RF signals is US PCS, and wherein:
the VCO operates between frequencies of 1716 MHz and 1769 MHz,
the divider divides by 8, and
the mixer is a high side SSB mixer.

37. The system of claim 12, wherein
the device includes a receiver, wherein
a band of received RF signals is IMT, and wherein:
the VCO operates between frequencies of 1688 MHz and 1736 MHz,
the divider divides by 4, and
the mixer is a high side SSB mixer.

38. The system of claim 12, wherein the device is included in a wireless communication transceiver.

39. The system of claim 12, wherein the device includes a transmitter.

40. The system of claim 39, wherein
a band of transmitted RF signals is US PCS, and wherein:
the VCO operates at frequencies between 1480 MHz and 1528 MHz,
the divider divides by 4, and
the mixer is a high side SSB mixer.

41. The system of claim 39, further comprising a first amplifier chain configured to operate in a first transmit frequency band, the amplifier chain being operatively coupled to an upconverter.

42. The system of claim 12, wherein the device includes a receiver, and further comprising an offset LO coupled to a third input of the mixer, wherein the mixer output provides an LO frequency for a transmitter.

43. The system of claim 12, wherein the first mixer input and the mixer output are differential.

44. The system of claim 12, wherein the device includes a receiver that incorporates differential signal paths.

45. The system for generating a local oscillator (LO) frequency in a multi-band direct conversion less communication device, the system comprising:
a voltage controlled oscillator (VCO);
a first divider having an input and an output produced by dividing an input signal, the input of the first divider being operatively coupled to the VCO;
a second divider having an input and an output produced by dividing an input signal, the input of the second divider being operatively coupled to the output of the first divider; and
a mixer having a first mixer input operatively coupled to the output of the first divider, a second mixer input operatively coupled to the output of the second divider, and an output.

46. The system of claim 45, further comprising a third divider operatively coupled to the mixer output.

47. The system of claim 45, wherein the VCO is a multi-band VCO.

48. The system for generating a local oscillator (LO) frequency in a multi-band direct conversion wireless communication device, the system comprising:
an LO generator having one or more configurations, each configuration being associated with at least one frequency band of RF signals and producing an output signal whose frequency is associated with the at least one frequency band of RF signals, and a mixer configured to mix a VCO frequency with a divided-down version of the VCO frequency; and
a configuration selection mechanism arranged to select a configuration associated with a chosen frequency band of RF signals.

49. The system of claim 48, wherein the LO generator is controlled based on the configuration selection mechanism.

* * * * *